United States Patent [19]
Sears et al.

[11] Patent Number: 5,888,213
[45] Date of Patent: Mar. 30, 1999

[54] METHOD AND APPARATUS FOR CONTROLLING AN EXTERNALLY POWERED PROSTHESIS

[75] Inventors: Harold H. Sears; Edwin K. Iversen; Kevin B. Hays, all of Salt Lake City; Arthur D. Dyck, Draper, all of Utah

[73] Assignee: Motion Control, Inc., Salt Lake City, Utah

[21] Appl. No.: 870,342

[22] Filed: Jun. 6, 1997

[51] Int. Cl.$^6$ .................................. A61F 2/54; A61F 2/70
[52] U.S. Cl. ............................................... 625/24; 623/57
[58] Field of Search .................................. 623/24, 25, 57; 414/5; 73/172

[56] References Cited

U.S. PATENT DOCUMENTS

| | | | |
|---|---|---|---|
| 3,509,583 | 5/1970 | Fraioli | 623/24 |
| 3,751,733 | 8/1973 | Fletcher et al. | 623/24 |
| 4,685,925 | 8/1987 | Childress et al. | 623/25 |
| 4,808,187 | 2/1989 | Patterson et al. | 623/25 |
| 4,831,531 | 5/1989 | Adams et al. | 414/5 X |
| 5,336,269 | 8/1994 | Smits | 623/25 |

FOREIGN PATENT DOCUMENTS

| | | | |
|---|---|---|---|
| 495047 | 8/1950 | Belgium | 623/25 |
| 467742 | 4/1975 | U.S.S.R. | 623/25 |

Primary Examiner—David H. Willse

[57] ABSTRACT

The present invention relates to improved controllers for externally powered prosthetic limb devices or similar extension devices such as orthotic devices or a sensor probe device. The improved controller operates a highly-efficient, compact, reliable and low-maintenance tactile force feedback system for translating a sensed pressure force from a prosthesis contacting an object or surface into a tactile sensory feedback pressure force to the user. The tactile force feedback system comprises at least one contact-responsive transducer which translates a sensed contact pressure from a portion of an extension device which contacts an object or surface into a corresponding electrical signal. The electrical signal is received by a microprocessor and processed into a proportional output voltage for producing a proportional torque from a motor. The motor is connected to a backdrivable planetary gearbox having a rotatable shaft connected to one end of a lever such that the gearbox output causes the lever to move in an arc segment. The opposite end of the lever has an attached tip member positioned to contact, and slightly depress, the user's skin when the shaft is forwardly rotated. The contact pressure of the tip member is, thus, applied to the user's skin with a contact pressure force proportional to the contact pressure force sensed by the contact-responsive transducer. In addition, the improved controller may permit the user to initiate self-calibration of various selected user-dependent operating parameters whenever desired and an adaptive filter for permitting user control of the rate of movement of the device such that smooth and steady control of either slow or more rapid prosthesis movement is achieved. The improved controller may also recognize multiple trigger patterns from signal input generated from either a single or from multiple control sites to effect switching between modes of operation, i.e., degrees of freedom, and/or functions.

15 Claims, 2 Drawing Sheets

METHOD AND APPARATUS FOR CONTROLLING AN EXTERNALLY POWERED PROSTHESIS

BACKGROUND OF THE INVENTION

1. The Field of the Invention

The present invention relates to electronic controllers for externally powered prosthetic limbs. More particularly, the present invention relates to an electronic controller which operates a tactile force feedback system for presenting electronic sensory information to a human user's intact tactile sense and which provides self-calibration means for adjusting selected user-dependent operating parameters to various environments and conditions.

2. The Relevant Technology

Prosthetic limbs are well known and utilized by thousands of amputees. Preferably, a prosthetic limb is durable and lightweight, requires little or no maintenance, and includes suitable mechanical drive units, e.g., motors, for effecting desired movements and functions, and a power source for the drive units, such as a battery or batteries. In addition, a prosthetic limb is preferably aesthetically pleasing in that its size and shape is similar to the natural limb being replaced. Within these constraints, a prosthetic limb should also have the capability to perform various useful functions of the missing limb efficiently and in a smooth and consistent manner. Although reproducibility of the performance, at will, of all human limb function and motions has remained an elusive goal, many advancements have been made in prosthesis technology.

Prosthetic devices are preferably controlled through self-contained electronic controller means such as a microprocessor or dedicated circuitry. Sophisticated controllers comprising multiple input acceptance means for permitting the processing of input commands from various sources including myoelectric inputs, potentiometer inputs, accelerometer inputs, touch inputs, and electronic sensory inputs such as force, pressure, or temperature sensor inputs, are known in the art. Controllers comprising multiple output deliverance means for permitting either output proportional to input, i.e., open loop operation, or output proportional to the difference between the actual result and a desired result, i.e., closed loop operation are also known in the art. Additional features, such as a power-saving mode for shutting down or cutting back the power to the motor under certain conditions, may also be advantageously incorporated into the controller.

Force Feedback

A problem with existing prostheses, however, is a lack of direct tactile sensory feedback relating to the force being exerted by the device upon a manipulated object or upon a surface. For example, a user of a prosthetic arm or hand does not receive direct tactile sensory feedback to permit control of the force being exerted upon manipulated objects. Similarly, a user of a lower limb prosthesis does not receive direct tactile sensory feedback to permit control of the pressure force being exerted upon a contacted surface. A prosthetic limb device typically has a force capability much greater than a natural limb. A prosthesis user can generally learn, through training and repetition, and with reliance upon visual and auditory input, a degree of control of the contact pressure force being applied by the device. This degree of control is very imprecise, however, and often much more force than necessary is applied. With respect to upper limb prostheses, handling of small, heavy, or fragile objects or performing precise tasks is often difficult. While perhaps less of a problem with respect to lower limb prostheses, improved control of the pressure force applied to surfaces while balancing to stand or lifting and lowering the prosthesis when changing positions or ambulating is desirable.

A potential approach to this problem with prosthetic hands was suggested by Peter P. Goulding in a thesis entitled "Extended Physiological Taction, Design and Evaluation of a Sensory Feedback System for Myoelectric Control of a Terminal Device," submitted to the faculty of the University of Utah, Department of Bioengineering, June, 1984. There, a pusher device, operated by a rack and pinion mechanism fixed to the shaft of a small DC motor with a gearhead transmission, was utilized to apply a pushing force to a portion of a user's skin. The pushing force proportionally corresponded to a pressure force applied by a prosthetic hook on an object being gripped by the hook. The pressure force applied by the hook moment arm between the tip and base was sensed by a strain gage transducer and the converted signal was used to control the force applied by the pusher device. Testing indicated that this type of direct tactile sensory feedback permitted test subjects to improve their control of the pressure force being applied to objects.

Another approach is disclosed in U.S. Pat. No. 4,808,187 issued to Patterson et al. Patterson et al. disclose use of piezoelectric crystal pressure transducers positioned on a myoelectric prosthetic hand or forearm to sense the level of pressure force applied to a grasped object. The sensed pressure force is converted to a corresponding signal which eventually results in a proportional effect on the hydraulic pressure within a pressurizable cuff encircling a portion of the user's remnant limb. In particular, the signal corresponding to the sensed pressure force is received by control circuitry for processing and the processed signal instructs a hydraulic motor to proportionally expand or contract a hydraulic cylinder which in turn increases or decreases the hydraulic pressure within the cuff. The user thus receives direct tactile feedback in the form of increases and decreases in constriction of the cuff upon the remnant limb in response to increases and decreases in pressure force sensed by the transducers.

Both the Goulding approach and the Patterson et al. approaches described above have practical problems. A rack-and-pinion translational mechanism requires a bulky and cumbersome apparatus having a shaft with a height equal to the movement of the pusher device. A hydraulic-powered mechanism is also bulky and cumbersome. In addition, hydraulic systems require careful calibration and substantial maintenance to ensure that the mechanism reliably and accurately responds to the sensed pressure force. Moreover, the inflatable/deflatable cuff encircling the user's remnant limb continually contacts a fairly substantial area of the underlying skin and could cause discomfort or deterioration over long periods of use. Also, the continuous contact may cause some adaptation to occur such that changes in the pressure are not as readily ascertained. Thus, the above-described approaches do not provide a highly-efficient, compact, reliable and low-maintenance tactile force feedback means for translating the sensed pressure force into a proportional tactile sensory feedback pressure force.

Mode Switching and Calibration

Externally powered myoelectric prosthetic devices have been developed which provide mode switching capability permitting a trained user to switch modes, i.e., degrees of freedom such as wrist pronation and supination, elbow flexion and extension, and hand closing and opening, with myoelectric signals from a particular muscle or muscle group control site. Thus, a skilled user may achieve the capability of smooth and rapid mode switching through selective flexure and contracture of specific muscles or muscle groups at a selected control site permitting a high level of function and control of the prosthetic device.

It will be appreciated that the specific limb being replaced and the particular user's physical and mental capabilities will affect the level of function which can be achieved and also the selection of the optimal prosthetic device and electronic controller features for that person. It will further be appreciated that user control is optimized when user-dependent operating parameters are calibrated to the particular user and conditions of desired use. In particular, individualized calibration of various operating parameters, such as gain and deadband for specific types of input, is typically performed by the prosthetist or other skilled person during the fitting and training period with a selected device.

An example of a prosthetic limb incorporating a sophisticated controller which permits switching between multiple degrees of freedom and/or multiple functions with myoelectric input from one or more muscle or muscle groups is found in U.S. Pat. No. 5,336,269, issued to Smits, incorporated herein by reference. Smits discloses a method and apparatus for switching between a plurality of degrees of freedom, e.g., wrist pronation and supination, elbow flexion and extension, and hand closing and opening. The apparatus comprises at least one electrode for picking up myoelectric signals of a muscle, circuitry for amplifying, full-wave rectifying and smoothing the myoelectric signals, an analog-to-digital converter for converting the received myoelectric signals to digital data, and a microcontroller having memory means and programming to operate the apparatus.

Depending on the patient, a particular muscle or muscle group contraction is selected as the trigger for switching degrees of freedom. The apparatus has two modes of operation, a training mode and an operating mode. During the training mode, a threshold is set by the prosthetist or other qualified trainer and the user is instructed to perform the selected contraction a number of times until an appropriate set of data points having a sum exceeding the specified threshold is obtained. These data points and a predetermined set of subsequent data points are used to generate a triggering pattern which is stored as a table in the microprocessor memory. During the operating mode, the myoelectric signals received are continuously analyzed by the microprocessor until recognition of the stored pattern triggers switching between degrees of freedom.

Existing prosthetic devices lack self-calibration means permitting the user to initiate re-calibration of user-dependent operating parameters to thereby adjust the sensitivity and performance of the device to various environments and conditions, both external and internal, which are encountered by the user. In particular, although some parameters may be individually calibrated by a prosthetist during a fitting and training period, as disclosed in the Smits patent, there are typically no means for permitting recalibration by the user when desired. Thus, the user cannot selectively re-calibrate the device to adjust the sensitivity for a particular desired type of use or for various environments or conditions encountered.

For example, with respect to the Smits disclosure, it will be appreciated that the value selected for the threshold of myoelectric activity during the training period is calibrated by the trainer/prosthetist on the basis of the nature of the myoelectric signals received from the particular trainee/user at the time of training. While this individualized calibration is very helpful and permits the trigger pattern to be determined under conditions specific for the user, the conditions and environment during the training period may differ somewhat from the user's condition and environment at other times. For example, depending on the user's location, factors such as elevation, temperature and humidity, etc. may change. These factors, as well as others such as fatigue or emotional state, may affect the user's physical and mental condition. Indeed, the user of a prosthesis, just like all humans, experiences a variety of environmental and circumstantial factors which affect performance of desired activities, and the corresponding myoelectric signals, at different times. Thus, calibration of user dependent input commands performed at the time of training may not provide the optimal performance at other times.

SUMMARY AND OBJECTS OF THE INVENTION

It is an object of the present invention to provide a controller for an externally powered prosthetic limb device or similar type of extension device, such as an orthotic device or a sensor probe device, which operates a highly-efficient, compact, reliable and low-maintenance tactile force feedback system for translating a sensed pressure force from the device contacting an object or surface into a tactile sensory feedback pressure force to the device user.

It is another object of the present invention to provide a controller for an externally powered prosthetic limb device having self-calibration means for permitting the user to initiate self-calibration of selected user-dependent operating parameters whenever desired. The self-calibration means are preferably automatically initiated by a predetermined activity such as turning on the device or performing a predetermined trigger movement. In addition, the self-calibration means preferably may be effected by a user interface program operable on a personal computer which can be connected to the controller.

It is yet a further object of the present invention to provide a controller for an externally powered prosthetic limb having adaptive filtering means for permitting smooth and steady control of either slow or more rapid prosthesis movement.

Yet another object of the present invention to provide a controller for an externally powered prosthetic limb having simultaneous switching means permitting recognition of multiple trigger patterns from signal input generated from either a single or from multiple control sites to effect switching between modes of operation, i.e., degrees of freedom, and/or functions.

These and other objects and features of the present invention will become more fully apparent from the following description and appended claims, or may be learned by the practice of the invention as set forth hereinafter. The present invention relates to improved controllers for externally powered prosthetic limb devices or similar extension devices such as orthotic devices or a sensor probe device. The improved controller operates a highly-efficient, compact, reliable and low-maintenance tactile force feedback system for translating a sensed pressure force from a prosthesis contacting an object or surface into a tactile sensory feedback pressure force to the user. In addition, the improved controller may include self-calibration means permitting the user to initiate self-calibration of various selected user-dependent operating parameters whenever desired and adaptive filter means for permitting user control of the rate of movement of the device such that smooth and steady control of either slow or more rapid prosthesis movement is achieved. The improved controller may also include simultaneous switching means for recognition of multiple trigger patterns from signal input generated from either a single or from multiple control sites to effect switching between modes of operation, i.e., degrees of freedom, and/or functions.

The tactile force feedback system operated by an improved controller in accord with the present invention comprises at least one contact-responsive transducer to translate a sensed contact pressure from a portion of an extension device which contacts an object or surface into an electrical signal corresponding to the sensed contact pressure. A strain gauge which senses bending moments has been found particularly suitable for use in the present invention. In an upper limb prosthetic device having a gripping member, the contact-responsive transducer could be placed on a surface or surfaces of the gripping member such that the pressure force applied to an object or surface is sensed. In a lower limb prosthetic device having a heel, toe, and/or shank member, a sensor could be positioned to sense heel loads, toe loads, or bending moments in the shank.

The contact-responsive transducer is connected to electronic controller means and processed into a proportional output voltage. Electronic controller means could, for example, comprise a microprocessor or suitable dedicated electronic circuitry. The electronic controller means preferably comprise field effect transistor drivers having very low "turn on resistance," i.e., a low voltage drop, to thereby ensure low power dissipation by the tactile force feedback system. The electronic controller means are connected to a motor capable of producing a torque proportional to the output voltage generated by electronic controller means. The motor is connected to a backdrivable planetary gearbox having a rotatable shaft such that the shaft is rotated forwardly by the torque output of the motor. The gearbox should be backdrivable such that, in the absence of applied torque and in the presence of a small backward force, the shaft will be backdriven, i.e., automatically rotate reversely, to a rest position.

The gearbox is connected to one end of a lever such that the gearbox output causes the lever to move in an arc segment. In this manner, the torque output of the motor and the rotational motion of the shaft is effectively transformed into a proportional near linear movement of the lever. The opposite end of the lever has an attached tip member. A mounting element is used to position the lever with respect to the extension device user such that the tip member contacts, and slightly depresses, the user's skin when the shaft is forwardly rotated. The contact pressure of the tip member is, thus, applied to the user's skin with a contact pressure force proportional to the contact pressure force sensed by the contact-responsive transducer.

The improved controller for a prosthetic limb device could also have simultaneous switching means for permitting separate recognition of multiple trigger commands from a single control site or to separately utilize input signals from more than one control site would be an advancement in the art. For example, the controller could utilize high input signals from a single control site to command a first mode of operation or a first function and low input signals from the same control site to command a second mode of operation or a second function. Alternatively, or additionally, the controller could process input signals from more than one control site to thereby command more than one mode of operation or function.

The improved controller for a prosthetic limb device could also have self-calibration means for permitting a user to initiate self-calibration of selected user-dependent operating parameters whenever desired. The self-calibration means allow the controller to adjust the sensitivity, and other operating parameters, of the device in an automatic fashion. The device user can initiate the self-calibration process whenever desired with a predetermined activity or the self-calibration means preferably may be effected by a user interface program operable on a personal computer which can be connected to the controller as, for example, with an interfacing cable device. Preferably, any operating parameter which depends upon input from the user can be re-calibrated during the self-calibration process.

The improved controller for an externally powered prosthetic limb of the present invention preferably also incorporates adaptive filtering means for permitting smooth and steady control of either slow or more rapid prosthesis movement. In particular, the electronic controller having adaptive filter means would adjust the amount of filtering in response to the nature of the input signal, such as the myoelectric signal.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to improved controllers for externally powered prosthetic limb devices or similar extension devices such as orthotic devices or a sensor probe device. The improved controller operates a highly-efficient, compact, reliable and low-maintenance tactile force feedback system for translating a sensed pressure force from a prosthesis contacting an object or surface into a tactile sensory feedback pressure force to the user.

In addition, the improved controller may include self-calibration means permitting the user to initiate self-calibration of various selected user-dependent operating parameters whenever desired and adaptive filter means for permitting user control of the rate of movement of the device such that smooth and steady control of either slow or more rapid prosthesis movement is achieved. The improved controller may also include simultaneous switching means for recognition of multiple trigger patterns from signal input generated from either a single or from multiple control sites to effect switching between modes of operation, i.e., degrees of freedom, and/or functions.

Force Feedback

A problem with existing extension devices, and particularly with prosthetic limb devices, is that the user does not receive direct tactile sensory force feedback relating to the pressure force being exerted by the device upon a manipulated object or upon a surface. Although a user can generally learn, through training and repetition, some degree of control of pressure forces applied by a device, the control is very imprecise. A user typically tends to rely to some degree upon associated visual and auditory input from the device to assist in determining the pressure force being applied. Thus, especially for users with other sensory disabilities, for example, persons who have impaired vision or hearing, control of the pressure force being applied may be difficult.

In particular, with respect to upper limb prostheses, effective tactile sensory feedback would permit improved control of the applied contact pressure force and facilitate handling of small, heavy, or fragile objects or performing precise tasks. Improved contact pressure force control would also benefit users of lower limb prostheses and facilitate gait training and other functions.

The improved controller of the present invention operates a highly-efficient, compact, reliable and low-maintenance tactile force feedback system for translating the sensed contact pressure force from a prosthesis device, or similar extension device, contacting an object or surface into a proportional tactile pressure force upon a portion of the device user's intact skin. In addition to devices for the disabled, systems which endeavor to present virtual reality information to a computer user or video game player could utilize the controller-operated tactile sensory feedback system of the present invention.

Figure 1:
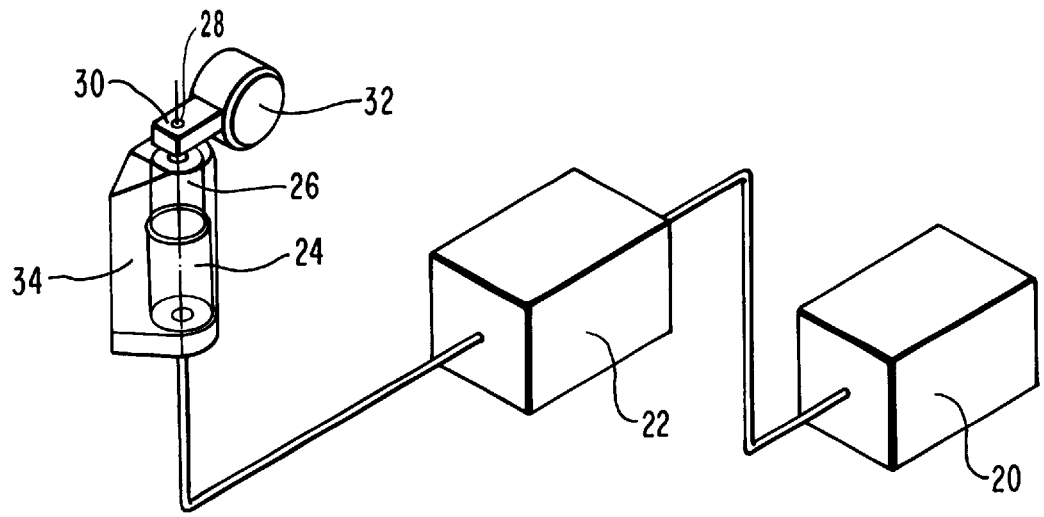
FIG. 1 is a schematic view of a presently preferred embodiment of the present invention.

FIG. 1 illustrates a schematic view of a tactile force feedback system operated by an improved controller in accord with the present invention. At least one contact-responsive transducer, illustrated schematically by reference box 20, is used to translate a sensed contact pressure from a portion of an extension device (not shown) which contacts an object or surface into an electrical signal corresponding to the sensed contact pressure. As described above, the extension device could be a prosthetic limb device, an orthotic device, a sensor probe device, or even a virtual reality or video game device.

Contact-responsive transducers are known in the art. A strain gauge which senses bending moments has been found particularly suitable for use in the present invention. In addition, pressure or force sensors are known. A temperature sensor could be used to sense a contact pressure force as a function of temperature. In an upper limb prosthetic device having a gripping member, contact-responsive transducer 20 could be placed on a surface or surfaces of the gripping member such that the pressure force applied to an object or surface is sensed. In a lower limb prosthetic device having a heel, toe, and/or shank member, a sensor could be positioned to sense heel loads, toe loads, or bending moments in the shank.

As shown in FIG. 1, contact-responsive transducer 20 is connected to electronic controller means, illustrated schematically by reference box 22. It may be desirable to have amplifying means (not shown) to amplify the electrical signal being transmitted to the electronic controller means. Electronic controller means 22 receives the electrical signal generated by contact-responsive transducer 20 and processes the signal into a proportional output voltage. Electronic controller means 22 are known in the art and could, for example, comprise a microprocessor or suitable dedicated electronic circuitry.

The electronic controller means preferably comprise field effect transistor drivers having very low "turn on resistance," i.e., a low voltage drop, to thereby ensure low power dissipation by the tactile force feedback system. Low power dissipation is important to avoid the need for cumbersome and bulky heat dissipator means. In addition, the electronic controller means preferably comprise automatic calibration means, described in detail below, to continuously re-calibrate the deadband for the contact-responsive transducer. In this manner, the controller can continually recalibrate the system such that very small sensor signals will result in tactile feedback to the user. Without such automatic calibration, the deadband would need to be set higher than the potential noise levels and, thus, may be too high for small sensor signals.

Electronic controller means 22 are connected to a motor 24 capable of producing a torque proportional to the output voltage generated by electronic controller means 22. Motor 24 is preferably compactly sized and lightweight with a high torque to inertia ratio such that high bandwidth feedback is obtained. Suitable motors include a miniature basket wound permanent magnet D.C. motor or a miniature brushless D.C. motor. These motors produce torques which are in direct proportion to the voltage supplied.

Motor 24 is connected to a backdrivable planetary gearbox 26 having a rotatable shaft 28 such that shaft 28 is rotated forwardly by the torque output of motor 24. Gearbox 26 is also preferably lightweight and compact in size, i.e., a miniature planetary gearbox. Gearbox 26 should be extremely efficient and have relatively low gear reduction such that the torque applied to the shaft is directly proportional to the gearbox output. Gearbox 26 should also be backdrivable such that, in the absence of applied torque and in the presence of a small backward force, shaft 28 will be backdriven, i.e., automatically rotate reversely, to a rest position.

Gearbox 26 is connected to one end of a lever 30 such that the gearbox output causes lever 30 to move in an arc segment. In this manner, the torque output of motor 24 and the rotational motion of shaft 28 is effectively transformed into a proportional near linear movement of lever 30. The opposite end of lever 30 has an attached tip member 32. A mounting element 34 is used to position lever 30 with respect to the extension device user (not shown) such that tip member 32 contacts, and slightly depresses, an intact portion of the user's skin when shaft 28 is forwardly rotated. The contact pressure of tip member 32 is applied to the user's skin with a contact pressure force proportional to the contact pressure force sensed by contact-responsive transducer 20. The backdriving force to return shaft 28 to a rest position, as described above, is provided by the tendency of the user's skin to return to a non-depressed position. In other words, the resiliency of the user's skin acts like a spring to provide sufficient force, in the absence of applied torque, to backdrive the shaft. In this manner, the need for more complicated and cumbersome bi-directional control of the motor/gearbox/shaft system is avoided.

The electronic controller preferably continuously monitors the magnitude of the electrical signal being received and, thus, the magnitude of the pressure contact force. In the absence of a sensed contact pressure, and preferably also when a sensed contact pressure remains constant for a predetermined time period, the electrical signal generated by contact-responsive transducer 20 is terminated causing electronic controller means 22 to cease the proportional voltage output, in turn causing motor 24 to cease the proportional torque production. When shaft 28 is no longer being forwardly rotated, no driving force is present to cause tip member 32 to press upon the user's skin. The tendency of the user's skin to return to a non-depressed position backdrives the gearbox such that lever returns to a position corresponding to the at rest position of shaft 28. In this position, tip member does not contact the user's skin. It has been discovered that the tactile sensory pressure force feedback is most effective when tip member 32 contacts skin overlying soft tissue rather than bone. It has further been discovered that less adaptation, i.e., decreased sensitivity to the contact pressure from tip member 32, occurs when tip member 32 comprises a relatively broad and rounded configuration rather than a sharp or pointed one.

Figure 2:
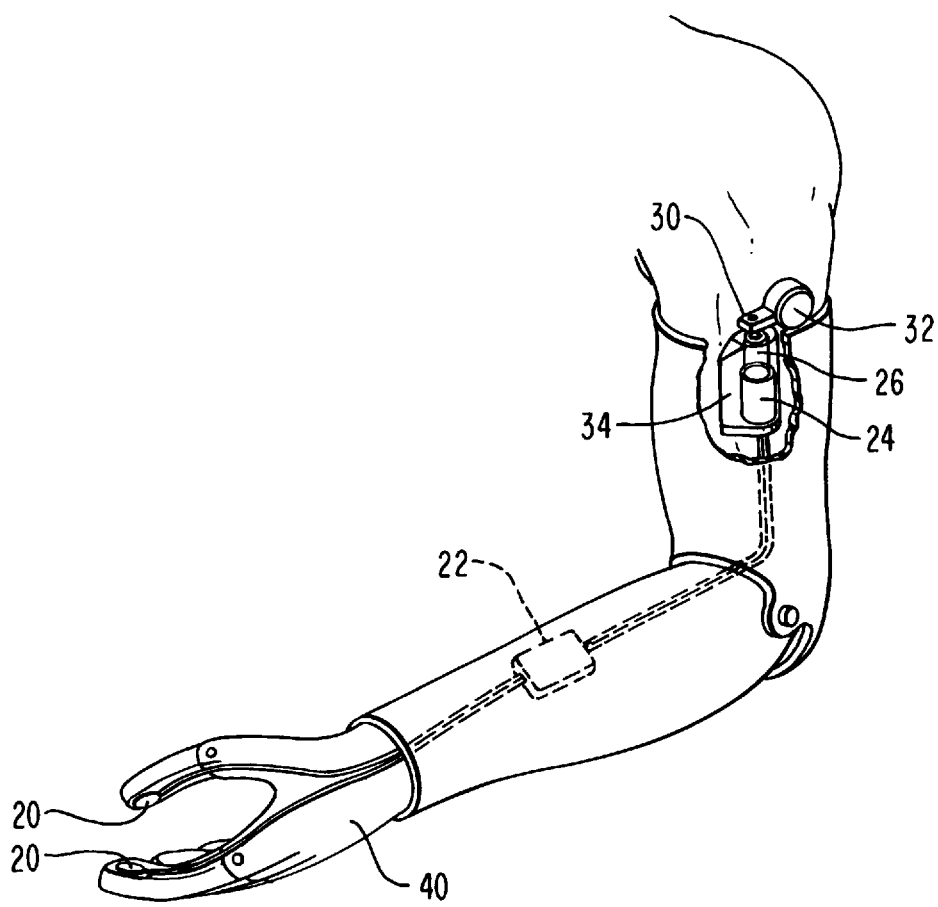
FIG. 2 is a perspective view of a presently preferred embodiment of the present invention.

FIG. 2 illustrates a perspective view of a presently preferred embodiment of an upper limb prosthetic device having an improved controller which operates a tactile force feedback system in accord with the present invention. The upper limb prosthetic device includes an artificial hand 40. A contact-responsive transducer 20, such as a semiconductor strain gauge, is preferably placed on at least one thumb or finger surface such that the contact pressure force when an object is gripped by hand 40 can be sensed. As shown, it is preferable to use more than one contact-responsive transducer 20.

As described above, each contact-responsive transducer 20 generates an electrical signal which is received by the connected electronic controller means 22. Electronic controller means 22 preferably comprises a microprocessor which converts the electrical signal into a proportional output voltage. The output voltage is received by motor 24, preferably a miniature basket wound permanent magnet D.C. motor, which produces a proportional torque. The torque rotates shaft 28 inside miniature planetary gearbox 26. Lever 30 is connected at one end to gearbox 26 such that lever 30 is moved in an arc segment by the gearbox output. Mounting element 34 holds motor 24 and gearbox 26. Mounting element 34 is securely positioned such that tip member 32, attached to the opposite end of lever 30, contacts a portion of the user's intact skin with a pressure force proportional to the pressure force sensed by the at least one contact-responsive transducer 20. Mounting element 34 is preferably secured to a portion of the prosthesis adjacent the desired position on the user's remnant limb as shown. Mounting element 34 might be secured directly to a position on the user distant from the prosthesis itself if such positioning is desired.

Also as described above, in the absence of a sensed contact pressure, and preferably also when a sensed contact pressure remains constant for a predetermined time period, the electrical signal terminates and motor 24 stops running. In the absence of a driving force, the tendency of the user's skin to return to a non-depressed position backdrives the gearbox 26 such that lever 30 returns to a position where tip member 32 does not contact the user's skin.

Mode Switching and Calibration Features

Conventional prosthetic devices capable of mode switching recognize a single myoelectric pattern as the trigger for switching degrees of freedom. Accordingly, when the user wishes to switch degrees of freedom, the single predetermined triggering muscle contraction is performed to switch the degrees of freedom in a predetermined order. If, for example, the prosthetic device has three degrees of freedom, e.g., elbow movement, wrist movement, and hand movement, the device will switch between these in a predetermined order, e.g., elbow to wrist to hand. Thus, if the device is in elbow movement mode, the trigger movement will switch the device to wrist movement mode and another trigger movement will switch the device to hand movement mode.

A desirable controller feature would be the capability to permit "simultaneous" mode switching, i.e., switching between multiple degrees of freedom and/or functions in a simultaneous, rather than sequential, manner. An improved controller for a prosthetic limb device having simultaneous switching means for permitting separate recognition of multiple trigger commands from a single control site or to separately utilize input signals from more than one control site would be an advancement in the art. For example, the controller could utilize high input signals from a single control site to command a first mode of operation or a first function and low input signals from the same control site to command a second mode of operation or a second function. Alternatively, or additionally, the controller could process input signals from more than one control site to thereby command more than one mode of operation or function.

A conventional feature of some controllers is to provide calibration means for permitting a prosthetist or other trained person to calibrate various user-dependent operating parameters during a training period. A problem with these existing devices, however, is the lack of self-calibration means permitting the user to initiate re-calibration of user-dependent operating parameters to thereby adjust the sensitivity and performance of the device to various environments and conditions, both external and internal, which are encountered by the user. Thus, an improved controller for a prosthetic limb device having self-calibration means for permitting a user to initiate self-calibration of selected user-dependent operating parameters whenever desired would be an advancement in the art.

The improved controller of the present invention preferably incorporates conventional calibration means and additionally provides self-calibration means permitting the user to initiate calibration of selected user-dependent operating parameters whenever desired. The self-calibration means allow the controller to adjust the sensitivity, and other operating parameters, of the device in an automatic fashion. The device user can initiate the self-calibration process whenever desired with a predetermined activity. For example, the self-calibration process may be programmed to initiate each time the device is turned on and/or each time a predetermined initiating activity such as, for example, performing two power-ons within 1 second, or performing a predetermined trigger movement, occurs. In addition, the self-calibration means preferably may be effected by a user interface program operable on a personal computer which can be connected to the controller as, for example, with an interfacing cable device.

Preferably, any operating parameter which depends upon input from the user can be re-calibrated during the self-calibration process. For example, the input may be from a myoelectric sensor, a force sensor for sensing tension in some portion of the device, or a pressure sensor which can be pressed by the user. The self-calibration means can be programmed to adjust the gain, i.e., amplification, for the selected input to a level required to produce a predetermined corresponding output level and to set the deadband, i.e., threshold, so that no output occurs when the input falls below an individualized level. The adjustment is based upon input sampled during a predetermined calibration period. The maximum input during the calibration period is used to set the gain and the minimum input is used to set the deadband. In addition to calibration of gains and deadbands for selected user-dependent input, a gain for rate of change for inputs used to command switching, e.g., myoelectric inputs, could also be included.

The improved controller for an externally powered prosthetic limb of the present invention preferably also incorporates adaptive filtering means for permitting smooth and steady control of either slow or more rapid prosthesis movement. In particular, the electronic controller having adaptive filter means would adjust the amount of filtering in response to the nature of the input signal, such as the myoelectric signal. If the user is endeavoring to move the prosthesis slowly, the controller would recognize this and utilize a low time constant filter such that many samples of the myoelectric signal are taken and averaged to give a very smooth and steady output response. If the amputee is endeavoring to move the prosthesis more rapidly, the controller would recognize this and utilize a high time constant filter such that fewer samples of the myoelectric signal are taken and averaged to give a quicker output response, i.e., to move the prosthesis more rapidly.

Other Features

In addition to operating a tactile force feedback system, the improved controller of the present invention preferably also incorporates desirable conventional features such as multiple input acceptance means for permitting the processing of input commands from various sources including myoelectric inputs, potentiometer inputs, accelerometer inputs, touch inputs, and electronic sensory inputs such as force, pressure, or temperature sensor inputs. Another desirable conventional feature preferably incorporated in the improved controller of the present invention is multiple output deliverance means for permitting either output proportional to input, i.e., open loop operation, or output proportional to the difference between the actual result and a desired result, i.e., closed loop operation.

Figure 3:
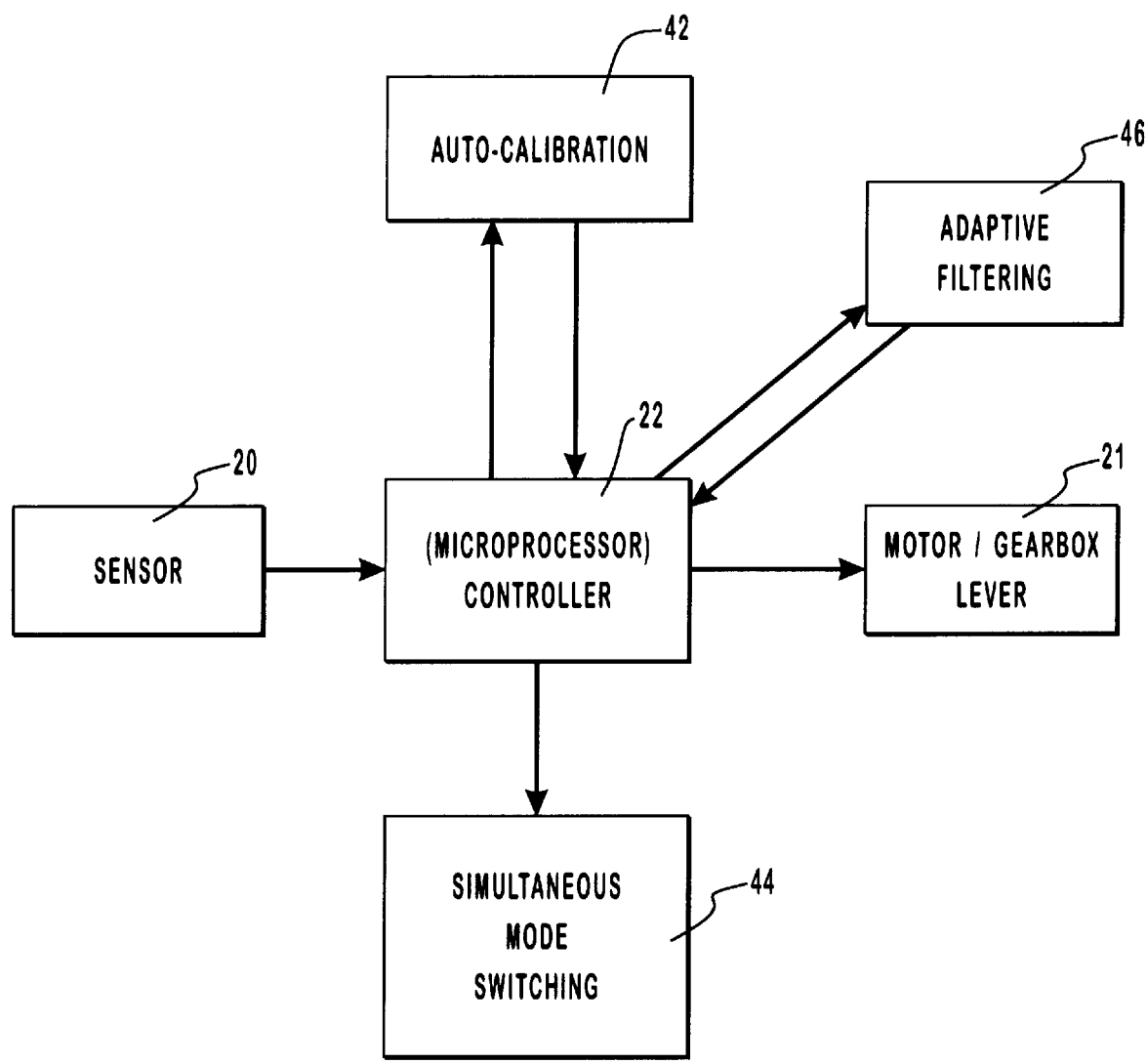
FIG. 3 illustrates a block diagram of a presently preferred embodiment of the present invention.

FIG. 3 illustrates a block diagram of a preferred embodiment of the improved controller of the present invention. Contact-responsive transducer 20 and electronic controller means 22 are shown with the same reference numerals as in FIGS. 1 and 2. As shown in FIG. 1, contact-responsive transducer 20 inputs data to electronic controller means 22. The remaining elements of the tactile force feedback system, i.e., the motor, shaft, planetary gearbox, lever, mounting element, and tip member are illustrated collectively by the output box designated 21. Auto-calibration means 42 and adaptive filtering means 46 are illustrated as a closed loop system with electronic controller means 22. Simultaneous mode switching 44 is shown as another output box.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A prosthetic device comprising:
   a socket configured for mounting the prosthetic device to a remnant limb of a user; and
   a tactile force feedback system for translating a sensed contact pressure from the prosthetic device and an object or surface with which the prosthetic device is brought into contact into a proportional tactile force upon the device user, said tactile force feedback system comprising:
   at least one contact-responsive transducer, said transducer being capable of sensing contact pressure and generating an electrical signal corresponding to the sensed contact pressure;
   an electronic controller for receiving said electrical signal corresponding to the sensed contact pressure and processing said electrical signal corresponding to the sensed contact pressure into a proportional output voltage;
   a motor connected to said electronic controller such that said voltage drives said motor, said motor producing a torque proportional to said output voltage;
   a planetary gearbox having a shaft connected to said motor such that said torque forwardly rotates said shaft, said gearbox being backdrivable such that said shaft reversely rotates to a rest position when said torque is absent;
   a lever having one end connected to said planetary gearbox such that said shaft rotational movement is translated to linear movement of said lever, said linear movement defining an arc segment;
   a tip member attached to an opposite end of said lever, said tip member having a first position when said shaft is in the rest position and a second position along said arc segment when said shaft is rotated forwardly; and
   a mounting element configured to position said lever such that said tip member contacts an intact portion of said user's skin in said second position at a location outside the socket, said contact being applied with a pressure proportional to the contact pressure sensed by said contact-responsive transducer.

2. The prosthetic device described in claim 1 said prosthetic device further comprising an artificial hand and wherein said at least one contact-responsive transducer is positioned on a thumb pad of said artificial hand.

3. The prosthetic device described in claim 2 further comprising at least one contact-responsive transducer positioned on a finger pad of said artificial hand.

4. The prosthetic device described in claim 3 wherein the at least one contact-responsive transducer comprises a semiconductor strain gauge which senses changes in force due to contact pressure between the artificial hand and an object or surface.

5. The prosthetic device described in claim 4 wherein the motor comprises a basket wound permanent magnet D.C. motor.

6. The prosthetic device described ir claim 5 wherein the electronic controller comprises field effect transistor drivers to ensure low power dissipation by the tactile force feedback system.

7. The prosthetic device described in claim 6 wherein the electronic controller further comprises automatic calibration means to continuously re-calibrate the deadband for the contact-responsive transducer to ensure sensitivity to small contact pressures.

8. The prosthetic device described in claim 7 wherein the electronic controller comprises a microprocessor.

9. The prosthetic device described in claim 8 wherein the tip member is rounded.

10. The prosthetic device described in claim 9 wherein the electronic controller further comprise self-calibration means for permitting the user to re-calibrate selected user-dependent operating parameters when desired.

11. The prosthetic device described in claim 10 wherein said electronic controller further comprises single and dual control site switching means.

12. The prosthetic device described in claim 11 wherein said electronic controller further comprises multiple input acceptance means for permitting the processing of input commands from various sources.

13. The prosthetic device described in claim 12 wherein said electronic controller further comprises multiple output deliverance means for permitting open loop operation and closed loop operation.

14. A prosthetic device as defined in claim 1 wherein the mounting element is configured to position the tip member on the remnant limb adjacent the prosthetic device.

15. A prosthetic device as defined in claim 1 wherein the mounting element is configured to position the tip member at a location distant from the prosthetic device.

* * * * *